United States Patent [19]

Rosenman et al.

[11] Patent Number: 5,669,935
[45] Date of Patent: Sep. 23, 1997

[54] ONE-WAY SUTURE RETAINING DEVICE FOR BRAIDED SUTURES

[75] Inventors: Daniel C. Rosenman, San Mateo, Calif.; Donald G. Hill, Hopatcong, N.J.

[73] Assignee: Ethicon, Inc., Somerville, N.J.

[21] Appl. No.: 508,600

[22] Filed: Jul. 28, 1995

[51] Int. Cl.[6] .................................................. A61B 17/04
[52] U.S. Cl. ........................................ 606/232; 606/151
[58] Field of Search ................................ 606/148, 151, 606/157, 158, 232, 139

[56] References Cited

U.S. PATENT DOCUMENTS 5,383,905  1/1995  Golds et al. .......................... 606/232
5,391,173  2/1995  Wilk .................................... 606/232

Primary Examiner—Michael Buiz
Assistant Examiner—Mark S. Leonardo
Attorney, Agent, or Firm—Hal Brent Woodrow

[57] ABSTRACT

A one-way adjustable suture retaining device suitable for use in arthroscopic surgery to secure one end of a braided suture comprising a frustum having an end and a base wherein a passage extends from the end to the base and the end has a plurality of slits extending from the end towards the base defining at least two flexible fingers and a process for using the retaining device to secure at least one end of a suture.

5 Claims, 1 Drawing Sheet

ONE-WAY SUTURE RETAINING DEVICE FOR BRAIDED SUTURES

FIELD OF THE INVENTION

This invention relates to a surgical device for retaining braided sutures. More particularly, this invention relates to a one-way adjustable suture retaining device suitable for use in arthroscopic surgery.

BACKGROUND OF THE INVENTION

Surgeons often must attach ligaments to bone, soft tissue to bone, or repair tears in ligaments in arthroscopic surgery. They prefer to use a suture to do this because of its small size and adequate strength. Surgeons secure the suture in place by tying knots with multiple throws. However, it is often difficult to tie knots arthroscopically because of the lack of access and limited visibility. Many of these procedures depend on extracoporial knotting to circumvent these difficulties. Unfortunately, extracoporial knotting is time consuming and difficult. Even with the advent of knot pushers and suture grabbers, it is still difficult for the surgeons to quickly tie arthroscopic knots. Thus, it would be a significant contribution to the art to provide a device that would replace suture knots in arthrisocpic surgical procedures.

SUMMARY OF THE INVENTION

We have discovered a one-way adjustable suture retaining device suitable for use in arthroscopic surgery to secure one end of a braided suture, wherein the device comprises a frustum having an end and a base wherein a passage extends from the end to the base and the end has a plurality of slits extending from the end towards the base defining at least one flexible fingers.

DETAILED DESCRIPTION OF THE INVENTION

Figure 1:
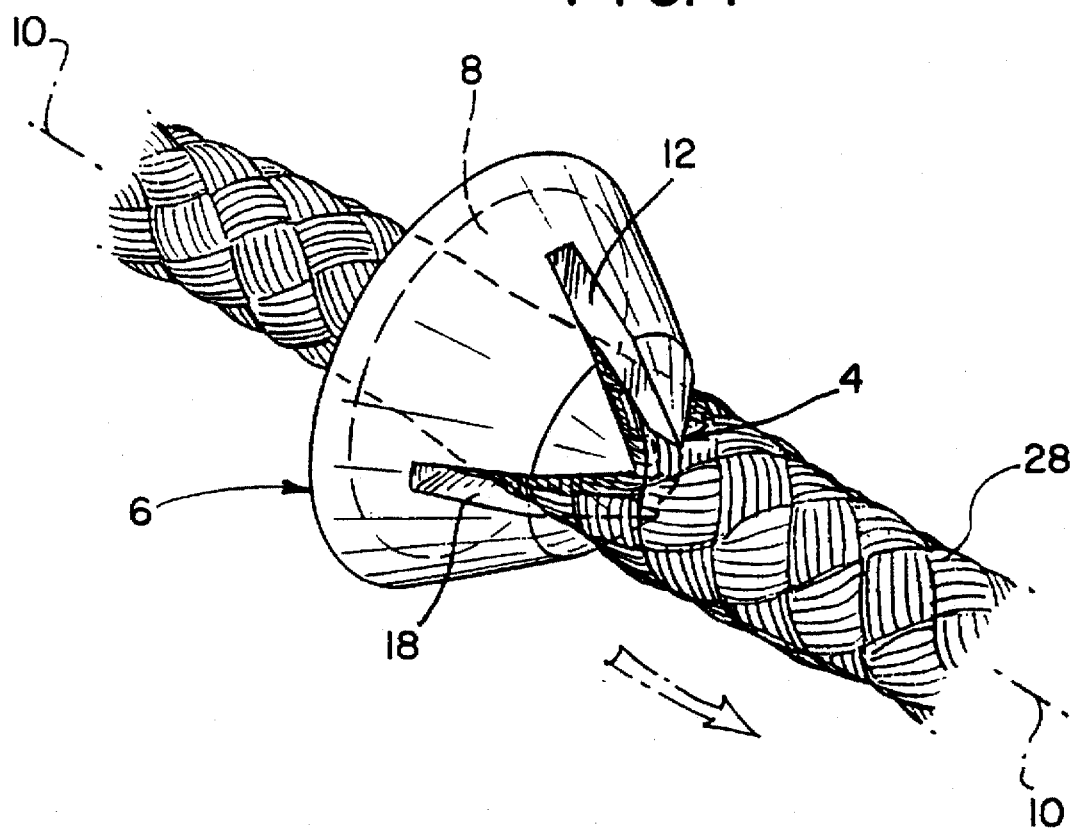
FIG. 1 is a perspective view of the suture retaining device engaged about a braided suture.
Figure 2:
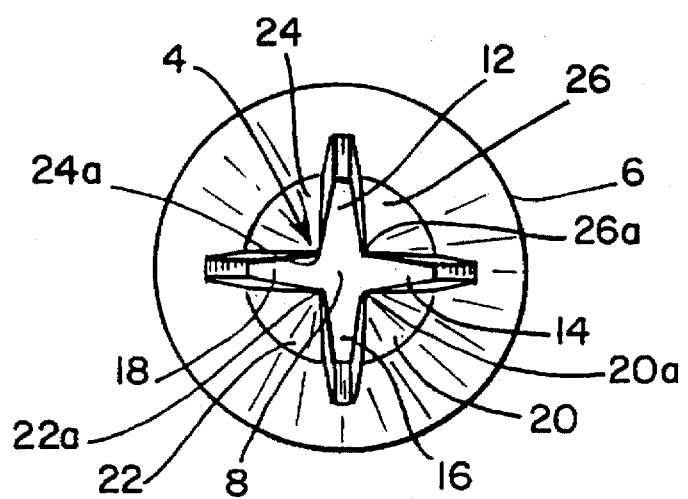
FIG. 2 is a frontal view of the suture retaining device.

Referring to FIG. 1 the one-way adjustable suture retaining device is a frustum having an end 4 and a base 6. Connecting the end 4 to the base is passage 8 which is substantially concentric about center line 10 which extends from the center of the base 6 to the center of the end 4. The end 4 has at least two slits 12 and 14 which extends generally from the end toward the base. Preferably end 4 will have four slits, 12, 14, 16 and 18, which define fingers 20, 22, 24 and 26 respectively, as shown in FIG. 2. The fingers 20, 22, 24 and 26 preferably have points 20a, 22a, 24a and 26a, which are adapted to engage braided suture 28 such that the suture cannot be advanced from the end 4 towards the base 6, but can be advanced from the base 6 toward the end 4 because of the flexibility of fingers 20, 22, 24, and 26. The suture retaining device should have a passage 8 of a sufficient diameter to allow a braided suture to easily pass through passage 8, but small enough to allow flexible fingers 20, 22, 24 and 26 to engage the braid when a suture in the passage 8 is moved towards the base 6.

In a proceedure, to secure one end of a suture, the suture would be passed through part of the tissue to be secured, then the suture would be passed through the passage 8 of the suture retaining device. The suture retaining device would be oriented on the suture so that the base would contact the tissue when advanced on the suture toward the tissue. The retaining device would be slid down the suture until the base contacted the tissue. Next the surgeon would pull the suture tight approximating the tissue together. As the surgeon progresses, he may use another suture retaining device to secure the other end of the suture thereby securing both ends of the suture. Preferably, the ends of the suture to which the suture knot retaining device are to be placed would have a simple knot tied in them to avoid the suture unravelling, thereby releasing the grip of the suture knot retaining device.

The retaining device of the invention can be made of any biocompatible material using conventional fabrication methods. The retaining device can be composed of various biocompatible metals, e.g. titanium, stainless steel, and tantalum, and polymeric materials. Preferred are bioabsorbable polymeric materials include but are not limited to aliphatic polyesters selected from the group consisting of homopolymers of epsilon-caprolactone, glycolide, lactide (including d, l, dl and meso) and para-dioxanone and copolymers of at least two thereof. Preferred non-absorbable polymers include but are not limited to materials selected from the group consisting of nylons, polyesters and polypropylene. All these materials have been demonstrated to be biologically acceptable when used as sutures or other implantable medical devices.

The preferred means for fabricating the retaining device from polymeric materials is to inject a polymer melt into an appropriately designed mold at process conditions conventionally employed for injection molding such polymer systems. After the polymer melt cools, the molded retaining device can be readily released from the mold, inspected, packaged and sterilized.

The retaining device may be sterilized by any of the well known sterilization techniques. The technique selected will depend to a great extent on the material used to make the retaining device. Suitable sterilization techniques include heat or steam sterilization, radiation sterilization (such as cobalt irradiation or electron beam), ethylene oxide, and other sterilization techniques well known in the art.

Having now described the present invention and certain specific embodiments thereof, it will be readily apparent to those skilled in the art that many variations and modifications may be made to the present invention without departing from the spirit and scope thereof.

We claim:

1. A sterile one piece, one-way adjustable suture retaining device suitable for use in arthroscopic surgery to secure a braided suture comprising a frustum having an end and a base wherein a passage extends from the end to the base the end has a plurality of slits extending from the end towards the base defining at least two flexible fingers that are configured to engage the braided suture when the braided suture is advanced from the end toward the base.

2. The sterile retaining device of claim 1 wherein the retaining device has four flexible fingers.

3. The sterile retaining device of claim 1 wherein a sterile braided suture is present in the passage.

4. The sterile retaining device of claim 1 wherein the suture retaining device is made of a biocompatible material selected from the group consisting of titanium, tantalum, homopolymers of ε-caprolactone, homopolymers of glycolide, homopolymers of lactide, homopolymers of p-dioxanone, copolymers of ε-caprolactone, copolymers of glycolide, copolymers of lactide and copolymers of p-dioxanone.

5. A process for securing one end of a braided suture that has been passed through a tissue relative to the tissue comprising placing a sterile one piece, one-way adjustable suture retaining device composed of a frustum having an end and a base wherein a passage extends from the end to the base and the end has a plurality of slits extending from the first end towards the base defining at least two flexible fingers, on the braided suture with the base oriented toward the tissue and advancing the braided suture retaining device relative to the braided suture by passing the braid suture through the passage for the base to the end until the base contacts the tissue, wherein the flexible fingers are configured to engage the braided suture when the braided suture is advanced from the end toward the base.

* * * * *